ial Number: 4,902,293
Date of Patent: Feb. 20, 1990

United States Patent [19]
Feaster

[54] INTRAOCULAR LENS WITH INFLATABLE HAPTIC

[76] Inventor: Fred T. Feaster, 800 8th Ave., Suite 234, Fort Worth, Tex. 76104

[21] Appl. No.: 337,260
[22] Filed: Apr. 13, 1989
[51] Int. Cl.⁴ .............................................. A61F 2/16
[52] U.S. Cl. ......................................................... 623/6
[58] Field of Search ........................................... 623/6

[56] References Cited

U.S. PATENT DOCUMENTS

| | | | |
|---|---|---|---|
| 3,711,870 | 1/1973 | Deitrick | 623/6 |
| 4,373,218 | 2/1983 | Schachar | 623/6 |
| 4,573,998 | 3/1986 | Mazzocco | 623/6 |
| 4,585,457 | 4/1986 | Kalb | 623/6 |
| 4,693,717 | 9/1987 | Michelson | 623/6 |

Primary Examiner—Ronald L. Frinks
Attorney, Agent, or Firm—Arthur F. Zobal

[57] ABSTRACT

The intraocular implant has a solid, non-inflatable, non-expandable, transparent optic member and an annular inflatable haptic member coupled to and circumferentially surrounding the outer periphery of the optic.

2 Claims, 2 Drawing Sheets

INTRAOCULAR LENS WITH INFLATABLE HAPTIC

BACKGROUND OF THE INVENTION

1. Field of the Invention

The invention relates to an intraocular lens for the human eye.

2. Description of the Prior Art

It has been a continuing goal in ophthalmology to develop an intraocular lens which can be placed through the smallest incision possible. There have been four basic approaches to intraocular lens design to accomplish this task:

1. The development of intraocular lens implants made of flexible materials which are foldable and can be implanted through a small incision in their smaller, folded state, to then have the implant unfold to its full size within the eye. Examples of such foldable designs are seen in the patents of Clayman U.S. Pat. No. 4,634,441 and Mazocoo U.S. Pat. No. 4,573,998.
2. The development of intraocular lens implants made of expandable materials which combine with water and which are implanted into the eye in their smaller, dehydrated state and then expand their volume once they are placed into the liquid-containing interior of the eye. Examples of this type of design are seen in patents U.S. Pat. Nos. 4,556,998 and 4,734,095 by Siepser, and U.S. Pat No. 4,710,194 by Kelman.
3. The development of intraocular lens implants containing two or more separate or movable pieces which require construction once placed within the eye. In some designs, the pieces are connected together but require repositioning (such as sliding) within the eye after implantation. Examples of this type of design are seen in U.S. Pat. No. 4,056,855 by Kelman, U.S. Pat. No. 4,636,210 by Hoffer, and U.S. Pat. No. 4,693,716 by Mackool.
4. Intraocular lens implants constructed to have an inflatable optic chamber or compartment which is expandable within the eye by means of injection of a suitable fluid-like material into the initially deflated chamber which then expands to produce the optic when completely inflated. This type of design is seen in U.S. Pat. No. 4,585,457 by Kalb, U.S. Pat. No. 4,693,717 by Michelson, and U.S. Pat. No. 4,373,218 by Schachar.

Presently, with currently available technology and materials, it appears that the inflatable type of intraocular lens, which can be implanted in its uninflated, rolled up or compressed condition and then re-expanded in the eye with injection of the proper fluid-like material, stands the best chance of being the implant design implantable through the smallest incision. However, all of the existing inflatable designs proposed to date involve inflating the optic and that is a very unacceptable design feature because, by involving the optic in the inflation process, the optical quality of the implant is necessarily affected by and dependent on the inflation process. More specifically, the optical quality and function will depend on the exact volume and quality of fluid-like material injected during the inflation process, and the skill of the surgeon performing the inflation. Also, the possibility of leaks from the inflated optic cavity might result in a change in the optic shape (and therefore its optical power) and forever threatens the future optical quality of the implant. This dependency of the optical quality (and therefore the implant's ability to restore good vision to the patient) on the inflation of the optic is a serious and permanent design flaw for any inflatable design involving the optic. This possible optical variability is also a potential problem in those designs in which the optic dimensions will change with the combination of the optic material with fluid, such as the designs of Siepser. To a lesser extent, the optical quality of foldable materials is a potential problem which has been largely overcome through materials development. Potentially, the problems of the inflatable optic designs can likewise be overcome, however, there does not appear to be a practical and usable solution available in the near future.

Therefore, it would be desirable to develop an implant design which incorporates the advantageous features of inflation for volume reduction/enlargement to allow implantation through the smallest incision possible, and yet has an optic of established and constant optical quality which is independent of the inflation mechanism. None of the described inflatable designs by Kalb, Schachar, Michelson or any other person incorporate inflatable haptics as part of their design. Their designs are essentially those of an inflatable or expandable optic and therefore contain the optical problems mentioned above.

SUMMARY OF THE INVENTION

It is an object of the invention to provide an intraocular implant comprising a non-inflatable and nonexpandable optic which is surrounded by a haptic which is inflatable by the injection of appropriate fluids or materials. In this way, the optic qualities are completely independent, stable and unchanging regardless of the success and quality of the inflation process. Difficulties with the inflation, should they occur, would affect only optic centration and not optic quality.

It is a further object of the invention to provide an intraocular implant for use as an artificial lens implant in a human eye and which comprises a non-inflatable, non-expandable, solid optic member having a central axis and an outer periphery and inflatable haptic means coupled to and circumferentially surrounding the outer periphery of the optic member.

In a further aspect, the inflatable haptic means comprises a flexible wall structure coupled to the outer periphery of the optic member defining an enclosed chamber for receiving a fluid for inflating the haptic means.

DESCRIPTION OF THE PREFERRED EMBODIMENTS

Figure 6:
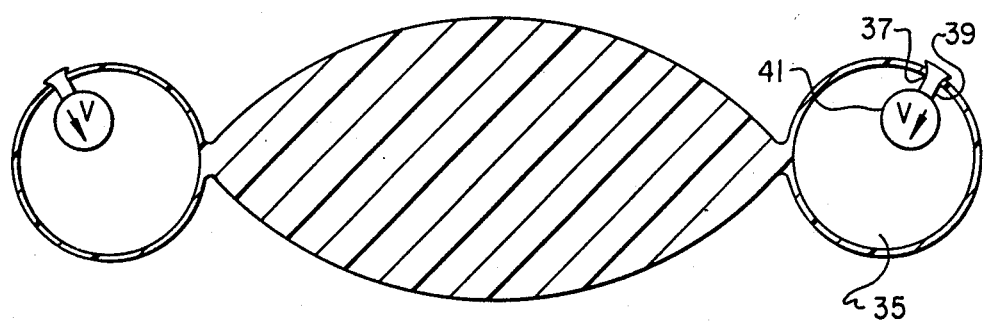
FIG. 6 is a cross-sectional view of the intraocular implant illustrating one-way valves for use for inflating the chamber of the haptic.

Referring now to the drawings the intraocular implant of the invention is identified at 21. It comprises a solid non-inflatable, non-expandable, transparent optic member 23 having a central axis 25 and an outer periphery 27. Coupled to and circumferentially surrounding the outer periphery 27 of the optic member 23 is a haptic member 31. The haptic member 31 comprises thin flexible wall structure 33 joined to and circumferentially surrounding the outer periphery 27 defining an enclosed annular chamber 35 for receiving a fluid such as a gas or a liquid or other fluid-like material for inflating the haptic member 31. As shown in FIG. 6, one or more small openings 37 may be formed through the wall 33 of the haptic means 31 to which are coupled tubes 37 with one-way valves 41 to allow the fluid to be injected into the chamber 35 for inflation purposes. The one-way valves 41 allow fluid to flow only into the chamber 35 and prevents the fluid from flowing out of the chamber 35.

Figure 1:
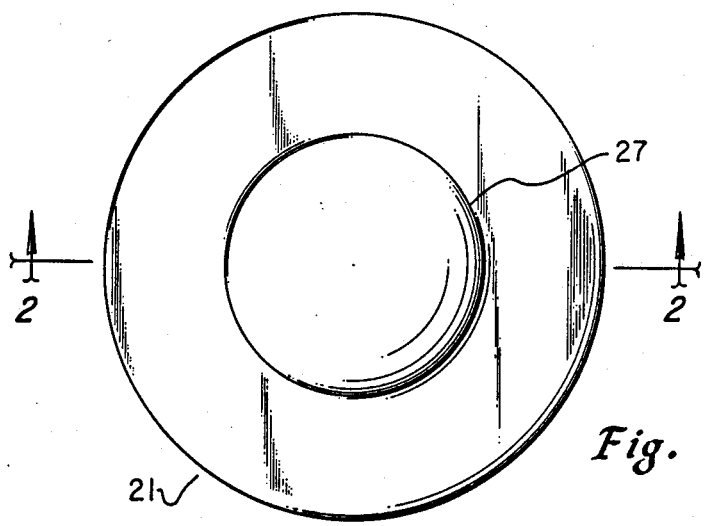
FIG. 1 is a plan view of the intraocular implant of the invention with the haptic uninflated.
Figure 2:
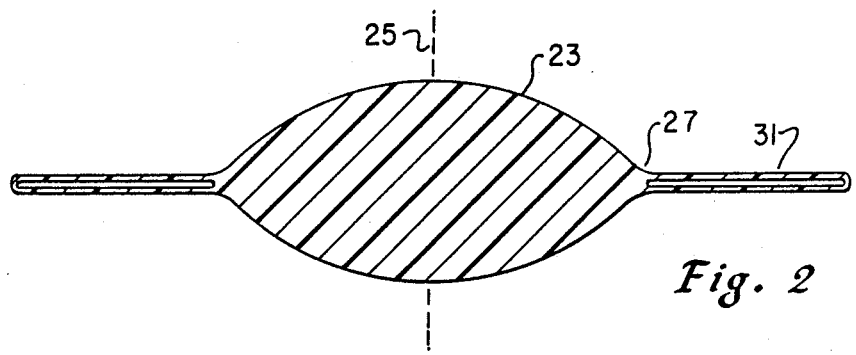
FIG. 2 is an enlarged cross-section of FIG. 1 taken along lines 2—2 thereof.
Figure 3:
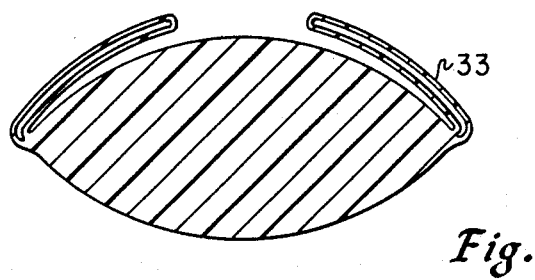
FIG. 3 is an enlarged cross-section of the intraocular implant of FIG. 1 with the uninflated haptic in a folded position.
Figure 5:
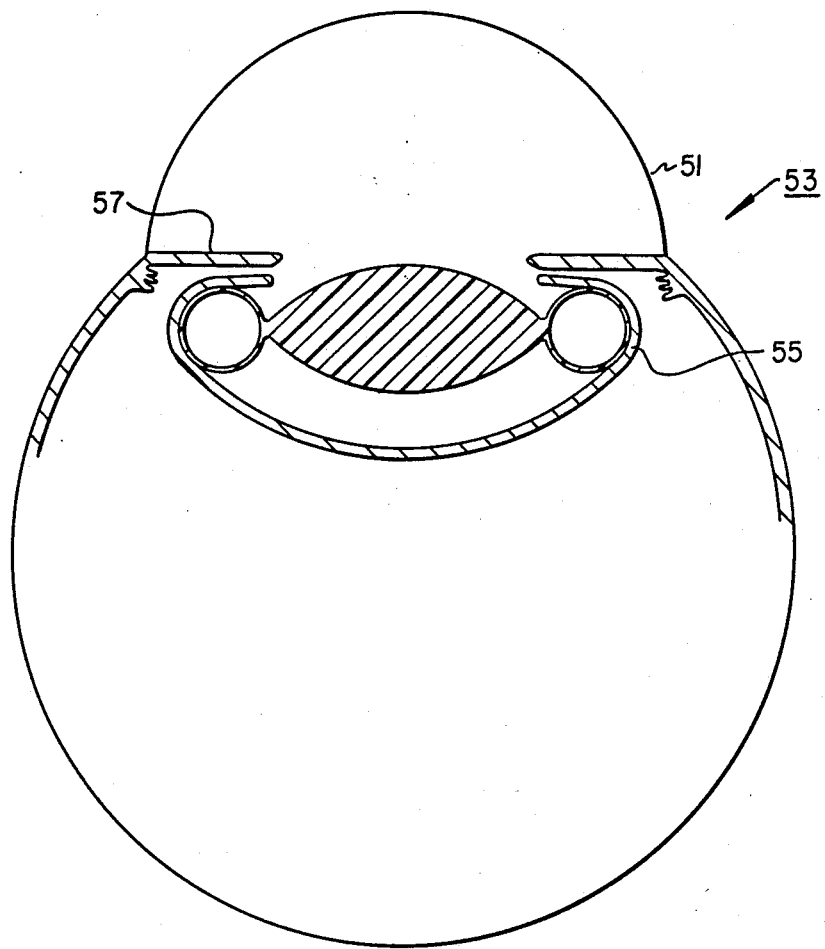
FIG. 5 illustrates the intraocular implant, in cross-section, with the haptic inflated and positioned within the capsular bag of a human eye.

The inflatable haptic member 31 is constructed to surround and attach to the outer periphery of the central optic 23. The haptic member 31 is formed of a thin flexible material which may also be an elastic or resilient material. It may be formed in its annular shape and then bonded to the outer periphery of the optic 31. In its uninflated condition (FIG. 2), it is essentially flat and can be folded over the optic 23 (FIG. 3) minimizing the volume of the implant 21 thereby permitting implantation through an incision size (formed through the corner 51 of the eye 53) determined primarily by the dimensions and volume of the optic. Once inside the eye, the implant is intended to be positioned entirely within the capsular bag 55 (behind the iris 57), where the haptics are then inflated for fixation and centration of the optic (FIG. 5). Therefore, it can be seen that the entire implant, comprised of the central uninflatable optic and surrounding inflatable haptic member (in its uninflated condition), will be implantable through a very small incision. Further, as mentioned, the problems with optic quality are totally avoided. Therefore, a lens of high and unvarying optical quality with small incision implantation capability is provided.

The haptic member 31 is inflated by injecting a suitably biocompatible fluid, which preferably is a liquid or other flowable liquid-like material but which may be a gas, into the chamber 35 which is ultimately defined and limited by the distensibility of the material comprising the haptic cavity wall 33. The injected fluid-like material or liquid may or may not develop a certain fixed shape or "harden". It can be seen that requirements of such a fluid-like material are considerably less stringent than requirements for materials which are injected into an optic space. That is to say, the biological properties of a fluid-like material which is injected into a haptic space are not as demanding as the biological properties of a material injected into an optic space and therefore are not as difficult to develop.

The fluid-like material may be injected into the inflatable haptic space 35 through the small conduit 39 with the aid of a small tubular needle with the one-way valve 41 allowing fluid flow in only one direction (toward the haptic chamber only) (FIG. 6). The material is injected until the haptic chamber is seen to be completely distended and the optic appropriately centered. In one embodiment, the one-way valve 41 may be of the type disclosed in U.S. Pat. No. 4,585,457, although other types of one-way valves may be used. Another mechanism for preventing material leakage is to employ only the conduit 39 and to seal its opening by heat, glue or other means after injection is completed. The wall of the inflatable haptic member is constructed of a thin, "foldable" or pliable material which may be an elastic or resilient material which defines the outer dimensions and configuration of the inflatable haptic member upon injection of a suitable biocompatible material. The wall material of the haptic member is nonpermeable to the injection material to prevent leakage of the injection material through the wall and into the eye.

Figure 4:
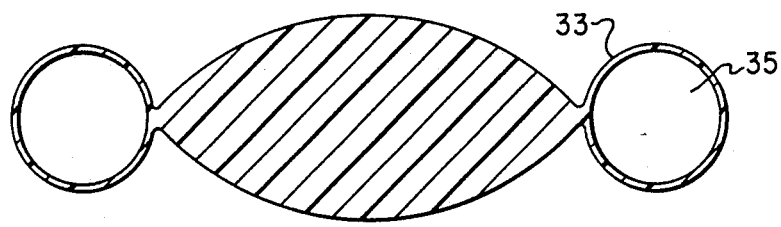
FIG. 4 is an enlarged cross-section of the intraocular implant of FIG. 1 with the haptic inflated.

In the preferred embodiment, the configuration of the haptic member 31 is annular such that the central uninflatable optic 23 is surrounded 360° peripherally and circumferentially by the haptic member 31 which when inflated is in the shape somewhat like that of an inflated inner tube. This will then give a complete circumferential type of contact between the haptic and the outer tissue (the lens capsule when placed within the capsular bag) which is recognized to be probably the most secure and desirable type of intraocular lens fixation attainable. The cross-sectional area of the inflated space 35 may be generally circular (FIG. 4), although it may vary considerably from this general configuration, particularly in decreasing the anterior/posterior dimension, while maintaining the radial dimension. Approximate dimensions for a preferred embodiment of the implant 21 comprises an optic measuring approximately 6 to 7 mm. in diameter, with the haptic cavity inflatable to give an overall diameter of the insert 21 of approximately 10–13 mm.

In one embodiment, the optic 23 may be formed of polymethylemethacrylate or other suitable materials such as a foldable silicone-like material. The haptic member 31 may be formed of a suitable silicone or silicone-like elastomers. The optic 23 and the haptic member 31 may be formed initially separately and the haptic member 31 located around the outer periphery 27 of the optic 23 and bonded or attached to the outer periphery. The fluid employed to inflate the haptic member 31 may be solutions of physiologic salts (index 1.33 to 1.44) and Dertran (index 1.39 to 1.4) or a polymeric material such as a Silastic as disclosed in U.S. Pat. No. 4,585,457. Other fluid type materials that may be employed to inflate the haptic member 31 are disclosed in U.S. Pat. No. 4,693,717.

In summary, a unique intraocular lens design incorporating a central uninflatable optic attached to and peripherally (circumferentially) surrounded by an inflatable haptic member which fixates and centers the optic within the eye (within the capsular bag) is provided. The implant is inserted into the eye in its uninflated configuration to minimize insertion wound size requirements, and then the haptic member is inflated by injection of a suitable biocompatible material into the haptic member once the implant is positioned loosely but completely within the capsular bag. This new design avoids the problems of optical quality inherent in any design in which the optic is inflated or expanded, yet still possesses the desirable features of a small incision lens with excellent fixation characteristics. This design solution to small incision implants provides a safer and more practical solution than those inflatable or expandable designs which involve the optic.

I claim:

1. An intraocular implant suitable for use as an artificial lens implant in a human eye comprising:
a non-inflatable, non-expandable optic member having a central axis and an outer periphery, and
inflatable haptic means coupled to and circumferentially surrounding said outer periphery of said optic member for engaging the tissue of a human eye and positioning said optic member in the eye when said haptic means is inflated.

2. The intraocular implant of claim 1, wherein:
said inflatable haptic means comprises flexible wall structure coupled to said outer periphery of said optic member and defining an enclosed chamber for receiving a fluid for inflating said haptic means.

* * * * *